United States Patent [19]

Schwartz

[11] B 3,984,914

[45] Oct. 12, 1976

[54] ORAL IMPLANT

[76] Inventor: Robert Schwartz, 1271 Westfield Ave., Rahway, N.J. 07065

[22] Filed: July 24, 1974

[21] Appl. No.: 491,501

[44] Published under the second Trial Voluntary Protest Program on January 13, 1976 as document No. B 491,501.

[52] U.S. Cl. ............................... 32/10 A; 3/1.9; 128/92 C
[51] Int. Cl.² ........................................ A61C 13/00
[58] Field of Search ................. 32/8, 10 A, 15; 128/92 C, 92 G; 3/1.9; 106/35

[56] References Cited

UNITED STATES PATENTS

| | | | |
|---|---|---|---|
| 3,729,825 | 5/1973 | Linkow et al. | 32/10 A |
| 3,787,900 | 1/1974 | McGee | 3/1.9 |
| 3,789,029 | 1/1974 | Hodosh | 128/92 C |

*Primary Examiner*—Russell R. Kinsey
*Assistant Examiner*—J. Q. Lever

[57] ABSTRACT

Improved endosseous and subperiosteal dental implants are obtained by providing the lower substructure of such implants with an adherent coating or reservoir of a calcium compound.

10 Claims, No Drawings

ORAL IMPLANT

BACKGROUND OF THE INVENTION

1 Field of the Invention

The present invention relates to improved dental implants. More particularly, the invention relates to an improved oral implant that resists body rejection by the invagination of epithelial tissue around the implant structure.

2. Description of the Prior Art

Oral implantology is an established dental procedure. The endosseous implant and subperiosteal implant act as a supporting structure or abutment for teeth which are to be replaced by either a fixed or removable prosthesis. In the case of the endosseous implant, a shaft, vent, pin, blade, screw, or helical coil (lower substructure) is inserted into the alveolar bone of the maxilla or mandible and the prosthesis is attached to a protruding upper abutment that is interconnected to the lower substructure. With a subperiosteal implant a specially formed substructure is normally seated on the alveolar bone and affixed thereto with small screws. The substructure is interconnected with an upper abutment member(s) which support a dental prosthesis. Many oral implants, especially endosseous implants, are unsuccessful because of the tendency of the body to reject the implant by the invagination of epithelial tissue around the substructure of the implant.

SUMMARY OF THE INVENTION

In accordance with the present invention, it has been discovered that the rejection of implants, especially endosseous implants, can be avoided by providing the substructure of the implant with a reservoir or at least a partial adherent external coating of a specific type of calcium compound. The presence of the calcium material in or on the implant substructure is believed to promote the formation by the body of a cementoid-type structure around the implant. Since the cementoid-type material is naturally formed the incidence of implant rejection is diminished.

DESCRIPTION OF THE PREFERRED EMBODIMENT

The first component of the improved oral implant of the present invention is an implant element that is fabricated from a biologically inert material. The expression "biologically inert material" is intended to include metallic, ceramic and organic polymeric substances that do not corrode or react with body tissues or body fluids. Useful materials of construction include gold and platinum alloys, titanium, tantalum, cobalt/chromium/molybdenum alloys, synthetic sapphire (alumina), annealed or unannealed stainless steel, cobalt/-chromium alloys sold under the trademark Vitallium, vitreous carbon sold under the trademark Vitredent, etc.

The implant element is composed of at least one upper abutment interconnected, preferably integrally connected, with a lower substructure. The lower substructure is adapted to be placed upon (subperiosteal implant) or inserted or submerged within (endosseous implant) alveolar bone of the maxillae or mandible. The precise configuration of the lower substructure portion of the implant element is not a critical feature of the instant invention. The lower substructure may be of any of the usual configurations. Depending upon anatomic limitations, the lower substructure portion of the implant element may be in the form of a spiral shaft, pin, blade, helical coil, etc. The lower substructure of a subperiosteal implant generally takes the form of an arch-shaped mesh structure that is adapted to be firmly seated upon the alveolar bone of the mandible. The lower substructure of such implants and the screws employed in the fixing of the substructure to the bone must both be fabricated from biologically inert materials. Further information concerning the configuration of implant elements and the materials used in their fabrication can be found in "Oral Implantology" edited by A. Norman Cranin, published by Charles V. Thomas, Springfield, Illinois (1970), the disclosures of which are herein incorporated by reference.

The second component of the improved oral implant of the present invention is a calcium compound-based coating system that is applied to at least a portion of the external surface of the substructure of the implant element or reservoir of a calcium compound. The essential constituents of the coating or reservoir material are non-toxic calcium compounds that are believed to release slowly calcium cations to the surrounding or adjoining bone structure in or on which the implant substructure is placed. Useful calcium compounds include (i) calcium hydroxide, (ii) calcium oxide (or other calcium compositions that are converted readily to calcium hydroxide upon contact with body fluids); (iii) calcium alcoholates, in particular compositions having the formula $Ca(OR)_2$ wherein R is an alkyl radical having from 1 to 6, preferably 1 to 3, carbon atoms; (iv) calcium salts of aliphatic monocarboxylic acids, in particular the lower monocarboxylic acids having less than 10, preferably less than about 5 carbon atoms per molecule, e.g. acetic acid, propionic acid; (v) calcium salts of a aliphatic hydroxymonocarboxylic acids, that is, compounds identical to those described in (iv) above except that the acid material has one or more hydroxy (-OH) functions per molecule, e.g. gluconic acid, levulinic acid, etc.; (vi) calcium salts of aliphatic hydroxypolycarboxylic acids, said acids having less than about 12 carbon a toms per molecule, at least two carboxy (—COOH) functions and at least one hydroxy function, e.g. D-saccharic acid; and (vii) mixtures thereof.

The calcium compounds that are employed herein are known materials and can be synthesized using conventional methods. For example, the above described calcium alcoholates can be prepared by reacting one mole of calcium metal with an excess of a straight or branched chain monohydric aliphatic alcohol (ROH) having from about 1 to 6, preferably from 1 to 3, carbon atoms per molecule. Materials such as calcium ethylate, calcium isopropylate, etc. are prepared by reacting metallic calcium with absolutely anhydrous methyl alchol, ethyl alcohol, isopropyl alcohol, etc. The formation of the calcium alcoholates proceeds more rapidly by contacting of metallic calcium with the alcohol reagent in the presence of an activator such as aluminum, or iodine. If an activator is used, it is desirable to remove activator impurities from the alcoholate product prior to use. The reaction of monohydric alcohols with calcium is initiated by slight heating; however, after the reaction is commenced, the reaction becomes exothermic and appropriate steps must be taken to remove excess heat from the reaction zone.

It is preferred that the external surface of the substructure of thee implant element be covered substantially completely with a continuous adherent coating of the calcium compound. A suitable calcium hydroxide coating may be obtained by admixing powdered calcium hydroxide or other applicable calcium compound with a surgical ointment or lubricant and applying the calcium compound/carrier mixture uniformly over the outer surface of the implant element substructure. Alternatively, the calcium compound may be dissolved in an appropriate solvent and the implant element refluxed in a boiling solution of the calcium compound to deposit a film of the calcium compound upon the implant. Small but sufficient quantities of calcium hydroxide can be deposited on an implant substructure by immersing the implant in a $Ca(OH_2)$/water solution or $Ca(OH_2)$/water/sugar solution at room temperature. Calcium alcoholate materials, which form calcium hydroxide upon contact with water, are applied conveniently to the implant element by immersing the implant element in a boiling solution of from 1 to 10 wt. % of the alcoholatee contained in anhydrous $C_1$ to $C_6$ aliphatic alcohol. Additional amounts of the above described calcium compound carrier mixture may be inserted into the bone opening prior to insertion of an endosseous implant or upon the alveolar bone, in the case of a subperiosteal implant.

Another mode contemplated for achieving the objects of the present invention is to provide the substructure of the implant element with a reservoir of the calcium compound. The desired reservoir(s) can be found in the substructure using various techniques. For example, the implant substructure may be provided with a porous structure by fabricating the substructure using powder metallurgy or selective chemical or electrolytic leaching. Alternatively, the substructure may be provided with a hollow core which communicates with the bottom of the implant substructure or may have fine holes drilled into the substructure or provided by plastic or wax fibrils if the implant is made by a "lost wax" casting technique. The reservoir(s) formed in the substructure are packed with a powder or paste or the above-identified calcium compounds to form the completed dental implant.

As noted above, the presence of the calcium compound in or on the implant element substructure when placed in position in contact with the patient's alveolar bone structure tends to promote the formation of a cementoid-type structure around the implant. This body-formed cementoid material serves, as experienced when calcium hydroxide is used in root canal therapy, to prevent the rejection of the implant by epithelial invagination. The calcium compound provided implant may be treated further with various ointments and/or lubricants to facilitate the placement of the implant and minimize post-operative edema, infection and discomfort. Further, the implant element may be sterilized prior to use.

What is claimed is:

1. An improved dental implant comprising an implant element fabricated from a biologically inert material, said implant element having an upper abutment and an interconnected lower substructure that is adapted to be placed upon or inserted within the alveolar bone of the maxillae or mandible, said substructure being provided with a reservoir or adherent coating of a calcium compound selected from the group consisting of calcium hydroxide, calcium oxide, calcium alcoholate, calcium salts of aliphatic monocarboxylic acids, calcium salts of aliphatic hydroxymonocarboxylic acids, calcium salts of aliphatic hydroxypolycarboxylic acids and mixtures thereof.

2. The implant of claim 1 wherein said calcium compound is calcium hydroxide.

3. The implant of claim 1 wherein said calcium compound is a calcium salt of an aliphatic monocarboxylic acid.

4. The implant of claim 1 wherein said calcium compound is a calcium alcoholate having the formula $Ca(OR)_2$ wherein R is an alkyl radical having from 1 to 6 carbon atoms.

5. The implant of claim 1 wherein said implant element is an endosseous implant.

6. The implant of claim 5 wherein said substructure is substantially completely covered with an adherent coating of calcium hydroxide.

7. The implant of claim 5 wherein said substructure is provided with a reservoir of calcium hydroxide.

8. The implant of claim 5 wherein said substructure is provided with a reservoir of a calcium alcoholate having the formula $Ca(OR)_2$ wherein R is an alkyl radical having from 1 to 6 carbon atoms.

9. The implant of claim 1 wherein said implant element is fabricated from a biologically inert metallic material.

10. The implant of claim 5 wherein said implant element is fabricated from a biologically inert metallic material.

* * * * *